United States Patent [19]

Earl et al.

[11] Patent Number: 4,982,000

[45] Date of Patent: Jan. 1, 1991

[54] PROCESS FOR PREPARING QUATERNARY AMMONIUM COMPOUNDS

[75] Inventors: Gary W. Earl, Bexley; Owen Portwood, Columbus, both of Ohio

[73] Assignee: Sherex Chemical Co., Inc., Ohio

[21] Appl. No.: 431,308

[22] Filed: Nov. 3, 1989

[51] Int. Cl.$^5$ .......................................... C07C 213/04
[52] U.S. Cl. .................................... 564/296; 564/292
[58] Field of Search ................................. 564/292, 296

[56] References Cited

U.S. PATENT DOCUMENTS

| | | | |
|---|---|---|---|
| 2,775,604 | 12/1956 | Zech | 260/404.5 |
| 3,104,933 | 9/1963 | Mendelsohn et al. | 3/85 |
| 3,272,712 | 9/1966 | Kalopissis et al. | 167/87 |
| 3,318,954 | 5/1967 | Curtin, Jr. | 260/567.6 |
| 3,342,840 | 9/1967 | Sobolev | 260/404 |
| 3,636,114 | 1/1972 | Tobler et al. | 260/567.6 |
| 3,879,464 | 4/1975 | Kalopissis et al. | 260/584 C |
| 3,932,495 | 1/1976 | Martinsson et al. | 260/567.6 M |
| 3,972,855 | 8/1976 | Martinsson et al. | 260/567.6 M |
| 4,239,391 | 7/1982 | Hoffmann et al. | 260/401 |
| 4,594,452 | 6/1986 | Remschuesset et al. | 564/292 |
| 4,675,180 | 6/1987 | Gunter | 564/292 |
| 4,812,263 | 3/1989 | Login | 564/292 |
| 4,814,506 | 3/1989 | Katayama et al. | 564/292 |

FOREIGN PATENT DOCUMENTS

| | | | |
|---|---|---|---|
| 3116087 | 11/1982 | Fed. Rep. of Germany | 564/292 |
| 61-106544 | 5/1986 | Japan | 564/292 |

*Primary Examiner*—James H. Reamer
*Attorney, Agent, or Firm*—Scully, Scott, Murphy & Presser

[57] ABSTRACT

The present invention is directed to a process for preparing a quaternary ammonium compound which comprises the reaction product of (a) a tertiary amine; (b) an alkylating agent characterized by the presence of a first member selected from the group consisting of hydroxyl and thiol radicals and a second member, a halogen atom, disposed on adjacent carbon atoms; and (c) an epoxy compound acting as an entraining reactant.

28 Claims, No Drawings

PROCESS FOR PREPARING QUATERNARY AMMONIUM COMPOUNDS

BACKGROUND OF THE INVENTION

1. Field of the Invention

The present invention relates to a process for preparing quaternary ammonium compounds from a tertiary amine and an alkylating agent containing a hydroxy or a thio group and a halogen group on adjacent carbon atoms. More specifically, the subject invention is directed to a process for preparing quaternary ammonium compounds from a tertiary amine and an alkylating agent containing a hydroxy or a thio group and a halogen group on adjacent carbon atoms in the presence of an epoxy entraining reactant.

2. Description of the Prior Art

Quaternary ammonium compounds have many commercial uses such as fabric softeners, anti-static agents, detergents, wetting agents, emulsifying agents, germicides, fungicides, textile assistants, textile lubricants, corrosion inhibitors, lubricant additives, mold-release agents, chemical intermediates, catalysts and the like.

A growing concern in the use of quaternary ammonium compounds in the above applications lies in their stability. That is, these compounds are very stable, comprising as they typically do four alkyl groups attached to a nitrogen atom. The non-biodegradable nature of these compounds poses a serious environmental problem, their disposability. The use of biodegradable quaternary ammonium compounds suggests itself as a solution to this growing problem. Indeed, biodegradable quaternary ammonium compounds are known in the art. These compounds are characterized by the inclusion of ester, ether and/or hydroxy groups. Their use, however, has been discouraged by the absence of commercially viable methods for their synthesis. Thus, while quaternary ammonium compounds containing hydroxy groups have been prepared, no commercially acceptable method has been developed for synthesizing these compounds.

Those skilled in the art are aware that quaternary ammonium compounds provided with hydroxy or thio functionality are subject to hydrolysis and thus degradation. However, the addition of this functionality into quaternary ammonium compounds is provided by alkylating agents in which the alkylating group is provided with hydroxyl or thiol functionality. The problem associated with this reaction resides in the long period of time required for this reaction to occur and, even then, in the low yield of the desired quaternary ammonium compound.

These two problems, slow reaction and low yield, are independent of whether the quaternary ammonium compound is an intermediate or the desired compound. That is, it applies whether the alkylating agent containing the biodegradable functionality is provided on a long chain alkylating agent to directly form the final product or whether this functionality is included in a short chain alkylating agent which is later reacted, by methods well known in the art, with a long chain alkyl group to produce the final quaternary ammonium compound product.

Several references teach the formation of quaternary ammonium compounds from long chain alkylating agents provided with hydroxy, ester or ether functionality. U.S. Pat. Nos. 3,104,933; 3,636,114; 3,879,464 and 3,972,855 establish the thermodynamic feasibility of these reactions. However, an analysis of the rate and yield of these reactions alert those skilled in the art of the difficulties associated with commercialization of these reactions.

The use of catalysts have been suggested to overcome the deficiencies of the prior art processes for synthesizing quaternary ammonium compounds. Thus, a variety of catalysts have been advanced for the alkylation of secondary and tertiary amines to produce quaternary ammonium compounds. Suggested catalysts include sodium hydroxide (U.S. Pat. No. 3,932,495) and the combination of sodium hydroxide and sodium bicarbonate (U.S. Pat. No. 3,318,954).

The use of epoxides and epihalohydrins in the formation of quaternary ammonium compounds is known in the art. For example, alkylthiohydroxypropyl quaternary ammonium halides are obtained by simultaneously reacting stoichiometric amounts of an alkylmercaptan, an epihalohydrin and a tertiary amine. These reactions are conducted at elevated temperature and typically require 16–24 hours at reflux to obtain 50–90% conversion to the product.

The quaternary ammonium halides of U.S. Pat. No. 2,775,604 are prepared in two distinct steps by reacting a polyhydroxylic compound with an epihalohydrin in the presence of a Lewis acid catalyst. The resultant glycerol halohydrin ether of the polyhydroxylic compound is reacted with a tertiary amine at elevated temperature in the absence of a catalyst.

Epoxides are used to purify quaternary ammonium compounds by reaction therewith. U.S. Pat. No. 3,468,816 teaches that this purification is the result of reduction of amine contamination.

In U.S. Pat. No. 3,272,712 a hydroxyester quaternary ammonium is prepared by reacting equimolar amounts of a fatty acid salt, an epihalohydrin and a secondary amine to form a tertiary amine which is then quaternized with dimethylsulfate or the like.

In contrast to the foregoing disclosures, U.S. Pat. No. 3,342,840 relates to the formation of hydroxy ester quaternary ammonium compounds by reacting a glycidyltrialkyl ammonium halide, itself a reaction product of an epihalohydrin and a tertiary amine, with a fatty acid.

A multistep process for preparing quaternary ammonium compounds is disclosed in U.S. Pat. No. 3,932,495 wherein an alkylated alcohol is reacted with excess epichlorohydrin to yield a hydroxyether chloride which, after removal of excess epichlorohydrin, is reacted with a secondary amine in the presence of a base to produce a quaternary ammonium compound.

Japanese Patent No. 49-1510 discloses a method of preparation of a quaternary ammonium compound that contains ester linkages by mixing a fatty acid with a tertiary amine to form the salt and then adding epichlorohydrin to complete the reaction.

A different method to produce quaternary ammonium compounds having ether and/or ester functionality is described in U.S. Pat. No. 4,339,391. That method involves esterification of a fatty acid with a tertiary amine followed by quaternization with a lower alkyl group.

Another class of quaternary ammonium compounds, recently recognized as having improved properties over other quaternary ammonium compounds, bis-quaternary ammonium compounds, also have not been commercially exploited to the extent they should because of the absence of a commercially viable process. Bis-quaternary ammonium compounds, the subject of U.S. Pat. Nos. 4,734,777 and 4,812,263 among others, are characterized by the presence of two nitrogen atoms in the molecules. The compounds are reported to possess excellent surface active properties.

The above remarks establish the absence in the art of processes to produce quaternary ammonium compounds having hydroxy, ester and/or ether functionality at a rate and in a yield that makes it commercially possible to exploit the desirable properties of these compounds.

SUMMARY OF THE INVENTION

A new process has now been discovered for the manufacture of biodegradable quaternary ammonium compounds, characterized by the presence of hydroxyl or thiol functionality on at least one of the groups attached to the nitrogen atom, permitting these quaternary ammonium compounds having the desirable properties discussed earlier, to be commercially exploited.

In accordance with the present invention a new process is provided for making quaternary ammonium compounds. In this process (a) a tertiary amine; (b) an alkylating agent, characterized by the presence of a first radical, said first radical selected from the group consisting of hydroxyl and thiol, and a second radical, a halogen, disposed on adjacent carbon atoms; and (c) an epoxy compound which serves as an entraining reactant.

DETAILED DESCRIPTION

The process of the present invention is directed to the preparation of quaternary ammonium compounds. These compounds are formed from the reaction product of a tertiary amine, an alkylating agent and an entraining reactant. The tertiary amine within the contemplation of the present invention has the structural formula

where $R^1$ is alkyl or hydroxyalkyl containing up to about 30 carbon atoms in which the alkyl chain may be interrupted by $-S-$, $-O-$, $-NR-$, $-^+NR_2-$, $CO_2-$ or carboxyamido; $R^2$ and $R^3$ are the same or different and are lower alkyl or lower hydroxyalkyl; and R is hydrogen, $C_1-C_4$ alkyl or $C_1-C_4$ hydroxyalkyl.

Preferably, $R^1$ is alkyl containing about 8 to about 24 carbon atoms; and $R^2$ and $R^3$ are the same or different and are $C_1-C_4$ alkyl.

More preferably, structural formula I is defined by $R^1$ being alkyl containing about 12 to about 18 carbon atoms; and $R^2$ and $R^3$ being the same or different and are $C_1-C_3$ alkyl.

Still more preferably, $R^1$ is alkyl containing about 14 to 18 carbon atoms; and $R^2$ and $R^3$ are the same or different and are $C_1-C_2$ alkyl. Even more preferably, $R^1$ and $R^2$ are methyl.

In another preferred embodiment the compound I has the structural formula I where $R^1$ and $R^2$ are the same or different and are alkyl or hydroxyalkyl containing up to about 30 carbon atoms in which the alkyl chain may be interrupted by $-S-$, $-O-$, $-NR-$, $-^+NR_2-$, $-CO_2-$ or carboxyamido; $R^3$ is lower alkyl or lower hydroxyalkyl; and R is hydrogen, $C_1-C_4$ alkyl or $C_1-C_4$ hydroxyalkyl.

Preferably, the tertiary amine having the structural formula I is characterized by $R^1$ and $R^2$ being the same or different and being alkyl containing between about 8 and about 24 carbon atoms; and $R^3$ being $C_1-C_4$ alkyl.

More preferably, $R^1$ and $R^2$ are the same or different and are alkyl containing between about 12 and about 18 carbon atoms; and $R^3$ is $C_1-C_3$ alkyl.

Still more preferably, the compound I is defined by $R^1$ and $R^2$ being the same or different and being alkyl containing between about 14 and about 18 carbon atoms; and $R^3$ being $C_1-C_2$ alkyl. Most preferably, $R^3$ is methyl.

The alkylating agent utilized in the process of the present invention is characterized by the presence of a first member, selected from the group consisting of hydroxy and thio radicals, and a second member, a halogen, disposed on adjacent carbon atoms. Preferably, the alkylating agent is defined by the structural formula

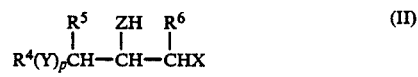

where $R^4$ is hydrogen, halogen, an alkyl or a hydroxyalkyl wherein the alkyl or hydroxyalkyl contains up to about 30 carbon atoms in which the alkyl or hydroxyalkyl chain may be interrupted by $-S-$, $-O-$, $-NR-$, $-^+NR_2-$, $-CO_2-$ or carboxyamido; Y is nitrogen, oxygen, sulfur, $CO_2$, $-CONH-$ or $CH_2$; Z is oxygen or sulfur; $R^5$ and $R^6$ are the same or different and are hydrogen, alkyl or hydroxyalkyl; p is 0 or 1 with the proviso that p is always 0 if $R^4$ is halogen; R is hydrogen, $C_1-C_4$ alkyl or $C_1-C_4$ hydroxyalkyl; and X is halogen.

More preferably, the compound having the structural formula II is defined by $R^4$ being hydrogen, a halogen or an alkyl containing between about 8 and about 24 carbon atoms; Y is oxygen or $CO_2$; Z is oxygen; $R^5$ and $R^6$ are the same or different and are hydrogen or methyl; and X is chlorine or bromine.

Still more preferably, in the compound having the structural formula II, $R^4$ is hydrogen or chlorine; Y is oxygen; $R^5$ and $R^6$ are hydrogen; and X is chlorine.

Most preferably, the compound having the structural formula II is 3-chloro-1,2-propanediol or 1,3-dichloro-2-propanol.

The entraining reactant, which during the formation of the quaternary ammonium compound dramatically increases the rate of reaction thus acting not only as a reactant but also as a catalyst, is an epoxy compound. The epoxy entraining reactant, which significantly decreases the time required to form the quaternary ammonium product compound in this reaction, preferably has the structural formula

where $R^7$ is hydrogen, $C_1-C_4$ alkyl, phenyl or benzyl; and $R^8$ is hydrogen, $C_1-C_4$ alkyl or $C_1-C_4$ haloalkyl.

More preferably, in defining the compound having the structural formula III, $R^7$ is hydrogen, $C_1-C_2$ alkyl or phenyl; and $R^8$ is hydrogen, $C_1-C_2$ alkyl or $C_1-C_2$ haloalkyl.

Still more preferably, the entraining reactant having the structural formula III is characterized by $R^7$ being hydrogen, methyl or phenyl; and $R^8$ being hydrogen, methyl or chloromethyl.

Most preferably, the entraining reactant is epichlorohydrin, 1,2-propylene oxide or ethylene oxide.

In a preferred embodiment the reactants discussed above are reacted in solution. The solvent utilized in this preferred embodiment, wherein the reaction occurs in solution, is a polar solvent. The preferred class of polar solvents employed in the process of this invention are protic solvents. Of the protic solvents, the alkanols are preferred. Alkanols having three to four carbon atoms are particularly preferred, with isopropanol being most preferred.

The thermodynamic conditions under which this reaction of a tertiary amine, an alkylating agent and an entraining reactant occurs, to produce a quaternary ammonium compound, includes a temperature in the range of between about 50° C. and about 150° C. and a pressure in the range of between atmospheric pressure and about 200 psi. Preferably, the temperature of this reaction is in the range of between about 70° C. and about 110° C. and the pressure is in the range of between atmospheric and about 100 psi. More preferably, the thermodynamic conditions of the reaction to produce the quaternary ammonium compound is a temperature in the range of between about 75° C. and about 100° C. and a pressure in the range of between atmospheric and about 75 psi. Even more preferably, the pressure of the reaction is the range of between atmospheric and about 50 psi. It is preferred that if the reaction occurs under elevated pressure, the elevated pressure be supplied by nitrogen.

The following examples are given to illustrate the process of the present invention. Because these examples are given for illustrative purposes only, the invention should not be limited thereto.

EXAMPLE 1

Preparation of the Alkylating Agent, 1-Stearoyl-3-chloro-2-propanol

Stearic acid (825 g., 3.0 moles), epichlorohydrin (416 g., 4.5 moles) and sodium carbonate (12 g.) were introduced into a 2-liter 4-necked round bottomed flask fitted with a mechanical stirrer, thermometer, temperature alarm sensor, dropping funnel and gaseous inlet and outlet tube. Nitrogen gas was sparged through the system to remove ambient air followed by heating the contents of the flask to 110° C. during which time the mechanical stirrer was activated.

After maintaining the contents of the flask for 11 hours at 110° C. the product was analyzed and was found to have had an acid value of 1.4 indicative of a 99% conversion of the stearic acid. The product was thereupon subjected to a vacuum, that is, the contents of the flask was subjected to a pressure of 1.0 mm Hg., whereupon any unreacted epichlorohydrin was removed with any other low boiling materials present in the flask. The contents of the flask were filtered resulting in the removal of the sodium carbonate. The resultant product was analyzed by both nuclear magnetic resonance (NMR) and thin layer chromatography (TLC) and found to be 1-stearoyl-3-chloro-2-propanol.

COMPARATIVE EXAMPLE 1

Preparation of 3-Stearoyl-2-hydroxypropylstearyldimethylammonium chloride

1-Stearoyl-3-chloro-2-propanol (386 g., 0.58 mole), made in accordance with the procedure of Example 1, stearyldimethylamine (172 g. 0.58 mole) and isopropanol (185 g.) were introduced into a 1-liter 4-necked round bottomed flask, equipped with the equipment provided with the 2-liter flask of Example 1. The total amine value of the contents of the flask was determined to be 43. Thereupon, the contents were subjected to a nitrogen gas sparge to flush out and remove any air. This was followed by heating the contents of the flask to 85° C.

The contents of the flask were heated for 8 hours at which time the product in the flask was analyzed and found to have a total amine value of 39. In that the initial total amine value was 43, total amine value determination established that the reaction proceeded only 10% to completion.

EXAMPLE 2

Preparation of 3-Stearoyl-2-hydroxypropylstearyldimethylammonium chloride

The product of Comparative Example 1 was contacted with epichlorohydrin (3 g., 0.03 mole) and again heated to 85° C. The epichlorohydrin-included contents of the flask were analyzed after heating for 4 hours and were found to have a total amine value of 9.6, indicative of an 80% conversion of amine starting reactant.

The contents of the 1-liter flask were again heated at 85° C. for an additional 4 hours at which time the contents were again analyzed to determine total amine value. The total amine value after 8 hours of reaction at 85° C. was found to be 1.6 which corresponds to a 96% conversion of the starting tertiary amine. An NMR analysis established the presence of 3-stearoyl-2-hydroxypropylstearyldimethylammonium chloride in a concentration such that 60% of the starting amine was converted to the desired product.

EXAMPLE 3

Preparation of 2,3-Dihydroxypropyldimethylstearylammonium chloride

To a 2-liter 4-necked round bottomed flask, fitted with a mechanical stirrer, thermometer, temperature alarm sense, dropping funnel and gaseous inlet and outlet tube, was added stearyldimethylamine (654 g., 2.11 moles), 3-chloro-1,2-propanediol (232 g., 2.11 moles) and isopropanol solvent (860 g.). These components were introduced into the flask under a nitrogen blanket provided by nitrogen gas introduced though the gaseous inlet tube. Eight grams of 1,2-propylene oxide, representative of 0.5% by weight, based on the total weight of the amine, the propanediol and the propylene oxide, was added dropwise through the dropping funnel while the temperature of the contents of the flask were maintained at 60° C. The temperature was raised to about 85° C. and maintained at that temperature for 5 hours. The pressure was atmospheric.

Upon completion of 5 hours, the isopropanol solvent was driven off at reduced pressure. The reaction mixture was analyzed and found to be 99% reacted. The product, 2,3-dihydroxypropyldimethylstearylammonium chloride, was characterized by its melting point, 65° C. –68° C. This analysis was confirmed by thin-layer chromatography. NMR analysis further confirmed the structure of the compound to be the titled quaternary ammonium compound.

EXAMPLE 4

Preparation of 2,3-Dihydroxypropyldimethylstearylammonium chloride

Example 3 was repeated but for the substitution of an elevated pressure, 60 psi, imparted by nitrogen gas, during heating at about 85° C., for the atmospheric pressure employed in Example 3.

The results of this example were substantially identical in all respects to those obtained in Example 3.

COMPARATIVE EXAMPLE 2

Prior Art Preparation of 2,3-Dihydropropyldimethylstearylammonium chloride

The experiment of Example 3 was identically repeated but for the omission of the entraining reactant, 1,2-propylene oxide. The product of this reaction was again 2,3-dihydropropyldimethylstearylammonium chloride. However, whereas 99% of the reactants were converted to the quaternary ammonium in 5 hours in Example 3, only 15% conversion of the reactants took place in this case.

This comparative example, conducted without 1,2-propylene oxide, was repeated except that the reaction was allowed to continue for 12.5 hours. At that time 45% of the theoretical yield to 2,3-dihydropropyldimethylstearylammonium chloride was obtained.

EXAMPLE 5

Preparation of 2-Hydroxypropylene-1,3-bis(dimethylstearylammonium chloride)

Stearyldimethylamine (90.6 g., 0.304 mole), 1,2-propylene oxide (1.3 g.) and isopropanol (37 g.) were introduced into a 2-liter flask of the type defined in Example 3. This mixture was heated to 75° C., and at this temperature and at atmospheric pressure 1,3-dichloro-2-propanol (19.7 g., 0.152 mole) was added dropwise through the dropping funnel over a period of 30 minutes. The mixture was maintained at this temperature and pressure for 9.5 hours. At the end of this period the reaction mixture as analyzed by amine titration and found to be 99.5% complete. That is, 99.5% of the titled quaternary ammonium compound that could be formed, based on the reactants charged, was synthesized.

COMPARATIVE EXAMPLE 3

Prior Art Preparation of 2-Hydroxypropylene-1,3-bis(dimethylstearylammonium chloride)

Example 2 was repeated but for the absence of 1,2-propylene oxide in the solution to which 2,3-dichloro-2-propanol was added dropwise. After 11 hours at 75° C. and atmospheric pressure, the reaction mixture was again analyzed by amine titration and found to have proceeded 50% to completion. That is, the quaternary compound, 2-hydroxypropylene-1,3-bis(dimethylstearylammonium chloride) was present in a concentration equivalent to a yield of 50% based on the amounts of the amine and the propanol compounds charged.

The above embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A process for preparing a quaternary ammonium compound comprising reacting:

(a) a tertiary amine having the structural formula

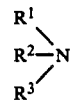

where $R^1$ is alkyl or hydroxyalkyl containing from about 8 to about 30 carbon atoms in which the alkyl group may be interrupted by —S—, —O—, —NR—, —$^+$NR$_2$, —CO$_2$— or carboxyamido; $R^2$ and $R^3$ are the same or different and are lower alkyl or lower hydroxyalkyl; and R is hydrogen, $C_1$–$C_4$ alkyl or $C_1$–$C_4$ hydroxyalkyl;

(b) an alkylating agent characterized by the presence of a first radical, said first radical selected from the group consisting of hydroxy and thio, and a second radical, a halogen atom, disposed on adjacent carbon atoms; and (c) an epoxy compound which serves as an entraining reactant.

2. A process in accordance with claim 1 wherein $R^1$ is an alkyl containing about 8 to about 24 carbon atoms; and $R^2$ and $R^3$ are the same or different and are $C_1$–$C_4$ alkyl.

3. A process in accordance with claim 2 wherein $R^1$ is an alkyl containing between about 12 to 18 carbon atoms; and $R^2$ and $R^3$ are the same or different and are $C_1$–$C_3$ alkyl.

4. A process in accordance with claim 3 where $R^1$ is an alkyl containing between about 14 to about 18 carbon atoms; and $R^2$ and $R^3$ are the same or different and are $C_1$–$C_2$ alkyl.

5. A process in accordance with claim 1 wherein said alkylating agent has the structural formula

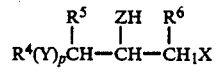

where $R^4$ is hydrogen, a halogen, an alkyl or a hydroxyalkyl, said alkyl or hydroxyalkyl containing up to about 30 carbon atoms in which the alkyl or hydroxyalkyl chain may be interrupted by —S—, —O—, —NR—, —$^+$NR$_2$—, —CO$_2$— or carboxyamido; Y is nitrogen, oxygen, sulfur, CO$_2$, —CONH—, or CH$_2$; Z is oxygen or sulfur; $R^5$ and $R^6$ are the same of different and are hydrogen, alkyl or hydroxyalkyl; p is 0 or 1, with the proviso that p is always 0 when $R^4$ is halogen; R is hydrogen, $C_1$–$C_4$ alkyl or $C_1$–$C_4$ hydroxyalkyl; and X is halogen.

6. A process in accordance with claim 5 wherein $R^4$ is hydrogen, halogen or an alkyl containing between about 8 to about 24 carbon atoms; Y is oxygen or CO$_2$;

Z is oxygen; $R^5$ and $R^6$ are the same or different and are hydrogen or methyl; and X is chlorine or bromine.

7. A process in accordance with claim 6 wherein $R^4$ is hydrogen or chlorine; Y is oxygen; $R^5$ and $R^6$ are hydrogen; and X is chlorine.

8. A process in accordance with claim 7 wherein the alkylating agent is 1,3-dichloro-2-propanol or 3-chloro-1,2-propanediol.

9. A process in accordance with claim 1 wherein said entraining reactant has the structural formula

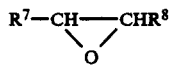

where $R^7$ is hydrogen, $C_1$-$C_4$ alkyl, phenyl or benzyl; and $R^8$ is hydrogen, $C_1$-$C_4$ alkyl or $C_1$-$C_4$ haloalkyl.

10. A process in accordance with claim 9 wherein $R^7$ is hydrogen, $C_1$-$C_2$ alkyl or phenyl; and $R^8$ is hydrogen, $C_1$-$C_2$ alkyl or $C_1$-$C_2$ haloalkyl.

11. A process in accordance with claim 10 wherein $R^7$ is hydrogen, methyl or phenyl; and $R^8$ is hydrogen, methyl or chloromethyl.

12. A process in accordance with claim 11 wherein the entraining reactant is selected from the group consisting of epichlorohydrin, 1,2-propylene oxide and ethylene oxide.

13. A process in accordance with claim 1 wherein said reactants are reacted in solution utilizing a polar solvent.

14. A process in accordance with claim 1 wherein said reaction occurs at a temperature in the range of between about 50° C. and about 150° C. and a pressure in the range of between atmospheric and about 200 psi.

15. A process in accordance with claim 14 wherein said temperature is in the range of between about 70° C. and about 110° C. and said pressure is in the range of between atmospheric and about 100 psi.

16. A process in accordance with claim 15 wherein said temperature is in the range of between about 75° C. and about 100° C. and said pressure is in the range of between atmospheric and about 75 psi.

17. A process for preparing a quaternary ammonium compound comprising reacting (a) a tertiary amine having the structural formula

where $R^1$ is alkyl or hydroxyalkyl containing up to about 30 carbon atoms in which the alkyl may be interrupted by —S—, —O—, —NH—, —$NR_2$— —$CO_2$— or carboxyamido; $R^2$ and $R^3$ are the same of different and are lower alkyl or lower hydroxyalkyl; and R is $C_1$-$C_4$ alkyl or $C_1$-$C_4$ hydroxylalkyl;

(b) an alkylating agent having the structural formula

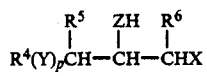

where $R^4$ is hydrogen, halogen, alkyl or hydroxyalkyl, said alkyl or hydroxyalkyl containing up to about 30 carbon atoms in which the alkyl or hydroxyalkyl chain may be interrupted by —S—, —O—, —NR—, —$^+NR_2$—, —$CO_2$— or carboxyamido; Y is nitrogen, oxygen, sulfur, $CO_2$ or $CH_2$; $R^5$ and $R_6$ are the same or different and are hydrogen, alkyl; Z is oxygen or sulfur; p is 0 or 1 with the proviso that p is always 0 if $R^4$ is halogen; R is hydrogen, $C_1$-$C_4$ alkyl or $C_1$-$C_4$ hydroxyalkyl; and X is halogen; and (c) an entraining reactant having the structural formula

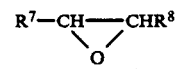

where $R^7$ is hydrogen, $C_1$-$C_4$ alkyl, phenyl or benzyl; and $R^8$ is hydrogen, $C_1$-$C_4$ alkyl or $C_1$-$C_4$ haloalkyl, said reaction occurring at a temperature in the range of between about 50° C. and about 150° C. and at a pressure in the range of between atmospheric and about 200 psi.

18. A process in accordance with claim 17 wherein $R^1$ is alkyl containing about 8 to about 24 carbon atoms; $R^2$ and $R^3$ are the same or different and are $C_1$-$C_3$ alkyl; $R^4$ is hydrogen, halogen or alkyl containing about 8 to about 24 carbon atoms; Y is oxygen or $CO_2$; $R^5$ and $R^6$ are the same or different and are hydrogen or methyl; Z is oxygen; X is chlorine or bromine; $R^7$ is hydrogen, $C_1$-$C_2$ alkyl or phenyl; and $R^8$ is hydrogen, $C_1$-$C_2$ alkyl or $C_1$-$C_2$ haloalkyl, said reaction occurring at a temperature in the range of between about 70° C. and about 110° C. and at a pressure in the range of between atmospheric and about 100 psi.

19. A process in accordance with claim 18 wherein $R^1$ is alkyl containing about 12 to about 18 carbon atoms; $R^2$ and $R^3$ are the same or different and are $C_1$-$C_2$ alkyl; $R^4$ is hydrogen or chlorine; Y is oxygen; $R^5$ and $R^6$ are hydrogen; X is chlorine; $R^7$ is hydrogen, methyl or phenyl; and $R^8$ is hydrogen, methyl or chloromethyl, said reaction occurring at a temperature in the range of between about 75° C. and about 100° C. and at a pressure in the range of between atmospheric and about 75 psi.

20. A process in accordance with claim 19 wherein $R^1$ is alkyl containing about 14 to about 18 carbon atoms; and $R^2$ and $R^3$ are methyl, said reaction occurring at a pressure in the range of between atmospheric and about 50 psi.

21. A process in accordance with claim 20 wherein $R^4$ is hydrogen; $R^7$ is hydrogen; and $R^8$ is methyl.

22. A process in accordance with claim 20 wherein $R^4$ is chlorine; $R^7$ is hydrogen; and $R^8$ is chloromethyl.

23. A process in accordance with claim 17 characterized by said reaction occurring in solution utilizing a polar solvent.

24. A process in accordance with claim 18 characterized by said reaction occurring in solution utilizing a protic solvent.

25. A process in accordance with claim 19 characterized by said reaction occurring in solution utilizing an alkanol as solvent.

26. A process in accordance with claim 20 characterized by said reaction occurring in solution utilizing an alkanol containing three or four carbon atoms as solvent.

27. A process in accordance with claim 26 where said alkanol is isopropanol.

28. A process in accordance with claim 1 where said tertiary amine has the structural formula

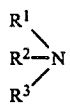
where $R^1$ and $R^2$ are the same or different and are alkyl or hydroxylalkyl containing up to about 30 carbon atoms in which the alkyl chain may be interrupted by —S—, —O—, —NR—, —$^+$NR$_2$—, —CO$_2$— or carboxyamido; $R^3$ is lower alkyl or lower hydroxyalkyl; and R is hydrogen, $C_1$-$C_4$ alkyl or $C_1$-$C_4$ hydroxyalkyl.
* * * * *